(12) United States Patent
Bronkalla et al.

(10) Patent No.: US 11,935,636 B2
(45) Date of Patent: Mar. 19, 2024

(54) DYNAMIC MEDICAL SUMMARY

(71) Applicant: MERATIVE US L.P., Ann Arbor, MI (US)

(72) Inventors: Mark D. Bronkalla, Waukesha, WI (US); Yufan Guo, San Jose, CA (US); Weber Marett, Hartland, WI (US)

(73) Assignee: Merative US L.P., Ann Arbor, MI (US)

( * ) Notice: Subject to any disclaimer, the term of this patent is extended or adjusted under 35 U.S.C. 154(b) by 795 days.

(21) Appl. No.: 16/396,259

(22) Filed: Apr. 26, 2019

(65) Prior Publication Data

US 2020/0342967 A1 Oct. 29, 2020

(51) Int. Cl.
| | |
|---|---|
| G16H 15/00 | (2018.01) |
| G16H 10/60 | (2018.01) |
| G16H 30/20 | (2018.01) |
| G16H 40/63 | (2018.01) |
| G16H 80/00 | (2018.01) |

(52) U.S. Cl.
CPC ............. *G16H 15/00* (2018.01); *G16H 10/60* (2018.01); *G16H 30/20* (2018.01); *G16H 80/00* (2018.01); *G16H 40/63* (2018.01)

(58) Field of Classification Search
CPC ........ G16H 15/00; G16H 10/60; G16H 30/20; G16H 80/00; G16H 40/63
USPC .......................................................... 705/3
See application file for complete search history.

(56) References Cited

U.S. PATENT DOCUMENTS

| | | | | |
|---|---|---|---|---|
| 10,629,303 B2 * | 4/2020 | Schulte | ................. | G16H 20/10 |
| 10,729,502 B1 * | 8/2020 | Wolf | ..................... | B25J 9/1661 |
| 2014/0324469 A1 | 10/2014 | Reiner | | |
| 2014/0350961 A1 | 11/2014 | Csurka et al. | | |
| 2015/0356270 A1 | 12/2015 | Devarakonda et al. | | |
| 2017/0185674 A1 | 6/2017 | Tonkin et al. | | |

(Continued)

OTHER PUBLICATIONS

Celi, Leo Anthony et al. "Disrupting Electronic Health Records Systems: The Next Generation." JMIR medical informatics vol. 3,4 e34. Oct. 23, 2015, doi: 10.2196/medinform.4192 (Year: 2015).*

(Continued)

*Primary Examiner* — Christopher L Gilligan
*Assistant Examiner* — Bennett Stephen Erickson
(74) *Attorney, Agent, or Firm* — Michael Best & Friedrich LLP (57) ABSTRACT

Methods and systems of summarizing medical data. One system includes an electronic processor configured to analyze medical data to extract a medical concept and a plurality of additional attributes of the medical concept and store the medical concept and the plurality of additional attributes. The electronic processor is configured to generate a first medical summary associated with the patient, where the first medical summary is based on the stored medical concept and at least a first additional attribute included in the stored plurality of additional attributes. The electronic processor is configured to receive a user interaction with the first medical summary. The electronic processor is configured to generate a second medical summary associated with the patient based on the user interaction, the second medical summary is based on the stored medical concept and at least a second additional attribute included in the stored plurality of additional attributes.

20 Claims, 6 Drawing Sheets

(56) References Cited

U.S. PATENT DOCUMENTS

| | | | | |
|---|---|---|---|---|
| 2019/0287665 A1* | 9/2019 | Forsberg | ................ | G16H 15/00 |
| 2019/0392926 A1* | 12/2019 | Koh | ........................ | G06F 40/40 |
| 2020/0294677 A1* | 9/2020 | Godinho | ................ | G16H 15/00 |
| 2020/0303074 A1* | 9/2020 | Mueller-Wolf | ........ | G16H 20/30 |
| 2020/0335188 A1* | 10/2020 | Ozeran | ................ | G06F 40/186 |

OTHER PUBLICATIONS

V. Tresp et al., "Going Digital: A Survey on Digitalization and Large-Scale Data Analytics in Healthcare," in Proceedings of the IEEE, vol. 104, No. 11, pp. 2180-2206, Nov. 2016, doi: 10.1109/JPROC.2016.2615052. (Year: 2016).*

W. Hsu et al., "A Case-Based Retrieval System Using Natural Language Processing and Population-Based Visualization," 2011 IEEE First International Conference on Healthcare Informatics, Imaging and Systems Biology, San Jose, CA, USA, 2011, pp. 221-228, doi: 10.1109/HIS (Year: 2011).*

* cited by examiner

Procedure date 6/12/2018

Procedure Information
Technique: Non-Enhanced Multidetector-Row Chest Computed Tomography. Axial (5mm; 1mm; 10mm MIPS); Coronal (3mm); and Sagittal (3mm) series were acquired.

Clinical Information
Indication: None.
Comparison: None

Findings:

Pulmonary Parenchyma and Airways: No pulmonary parenchymal or airway process is present.

Pleural Space: No pleural fluid or thickening is present.

Heart and Pericardium: The left ventricle is normal in size. No pericardial fluid or thickening is present.

Mediastinum and Hila: No mediastinal mass is present. No enlarged lymph nodes are present.

Thoracic Vessels: No significant vascular abnormality is present.

Osseous Structures and Chest Wall: No pathologic osseous or soft-tissue process is present.

Upper Abdomen: No pathologic process is present in the imaged portion of the upper abdomen Additional findings: None.

Impression: Normal

6/12/2018   CT Chest wo Contrast   Normal

*FIG. 6A*

6/12/2018  6/12/2018    CT Chest wo Contrast   Normal; No significant vascular abnormality is present

*FIG. 6B*

6/12/2018  6/12/2018    CT Chest wo Contrast Normal; No pulmonary parenchymal or airway process is present. No pleural fluid or thickening is present. <u>The left ventricle is normal in size</u>. No pleural fluid or thickening is present. The left ventricle is normal in size. No significant vascular abnormality is present

*FIG. 6C*

DYNAMIC MEDICAL SUMMARY

FIELD

Embodiments described herein relate to a dynamic medical summary, and more particularly, to analyzing medical data associated with a patient and generating a dynamic medical summary relating to the medical data associated with the patient.

SUMMARY

When presenting medical data in a summarized or synoptic fashion one goal is to provide the most relevant medical information to a user, such as a reviewing clinician or a physician. Accordingly, in some systems, the most "important" and "relevant" data may be presented to the user within a medical summary and the non-relevant data or noise may be removed or hidden. However, what is relevant to one user may not be relevant to another user even for the same patient, and what is relevant for one user may vary from patient to patient based on the complexity of the patient, the variety of problems or comorbidities present, or the like.

To solve these and other problems, embodiments described herein provide methods and systems for summarizing medical data by allowing a user to tune or adjust one or more parameters associated with the relevancy of medical data included in a medical summary to suit the user's current needs, where there are multiple dimensions of relevancy, such as body part or region, disease state, the source of information, and the like.

For example, one embodiment provides a system of summarizing medical data. The system includes at least one electronic processor configured to receive medical data associated with a patient, analyze the medical data to extract a medical concept and a plurality of additional attributes of the medical concept, and store the medical concept and the plurality of additional attributes of the medical concept. The at least one electronic processor is also configured to generate a first medical summary associated with the patient by accessing the stored medical concept and the stored plurality of additional attributes of the medical concept, wherein the first medical summary is based on the stored medical concept and at least a first additional attribute included in the stored plurality of additional attributes of the medical concept. The at least one electronic processor is also configured to transmit the first medical summary to a user device for display to a user via a display device of the user device and receive a user interaction with the first medical summary via an input mechanism of the user device. The at least one electronic processor is also configured to generate a second medical summary associated with the patient based on the user interaction with the first medical summary by accessing the stored medical concept and the stored plurality of additional attributes of the medical concept, wherein the second medical summary is based on the stored medical concept and at least a second additional attribute included in the stored plurality of additional attributes of the medical concept, wherein at least a portion of the second medical summary includes different medical data than the first medical summary. The at least one electronic processor is also configured to transmit the second medical summary to the user device for display to the user via the display device of the user device.

Another embodiment provides a method of summarizing medical data. The method includes receiving medical data associated with a patient, analyzing, with an electronic processor, the medical data to extract a medical concept and a plurality of additional attributes of the medical concept, and storing the medical concept and the plurality of additional attributes of the medical concept. The method also includes generating, with the electronic processor, a first medical summary associated with the patient by accessing the stored medical concept and the stored plurality of additional attributes of the medical concept. The method also includes transmitting, with the electronic processor, the first medical summary to a user device for display to a user via a display device of the user device and receiving a user interaction with the first medical summary via an input mechanism of the user device, wherein the user interaction is a selection of at least one additional attribute included in the stored plurality of additional attributes of the medical concept. The method also includes generating, with the electronic processor, a second medical summary associated with the patient based on the user interaction with the first medical summary by accessing the stored medical concept and the stored plurality of additional attributes of the medical concept, wherein the second medical summary is based on the stored medical concept and the selection of the at least one additional attribute included in the stored plurality of additional attributes of the medical concept and wherein at least a portion of the second medical summary includes different medical data than the first medical summary. The method also includes transmitting, with the electronic processor, the second medical summary to the user device for display to the user via the display device of the user device.

Another embodiment provides a non-transitory, computer-readable medium storing instructions that, when executed by an electronic processor, perform a set of functions. The set of functions includes receiving medical data associated with a patient, analyzing, with an electronic processor, the medical data to extract a medical concept and a plurality of additional attributes of the medical concept, and storing, with the electronic processor, the medical concept and the plurality of additional attributes of the medical concept. The set of functions also includes generating, with the electronic processor, a first medical summary associated with the patient by accessing the stored medical concept and the stored plurality of additional attributes of the medical concept, wherein the first medical summary is based on the stored medical concept and at least a first additional attribute included in the stored plurality of additional attributes of the medical concept. The set of functions also includes transmitting, with the electronic processor, the first medical summary to a user device for display to a user via a display device of the user device and receiving a user interaction with the first medical summary via an input mechanism of the user device, wherein the user interaction includes a selection of at least a second additional attribute included in the stored plurality of additional attributes of the medical concept. The set of functions also includes generating, with the electronic processor, a second medical summary associated with the patient based on the user interaction with the first medical summary by accessing the stored medical concept and the stored plurality of additional attributes of the medical concept, wherein the second medical summary is based on the stored medical concept, the first additional attribute, and the second additional attribute and wherein at least a portion of the second medical summary includes different medical data than the first medical summary. The set of functions also includes transmitting, with the electronic processor, the second medical summary to the user device for display to the user via the display device of the user device.

Other aspects of the embodiments described herein will become apparent by consideration of the detailed description and accompanying drawings.

Other aspects of the embodiments described herein will become apparent by consideration of the detailed description.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used herein, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

As described above, when summarizing medical information for a given patient it is desired to present the most relevant medical information within a single screen (or multiple screen, such as two screens) of a medical summary for the user. Accordingly, the most "important" and "relevant" medical data may be presented to the user and non-relevant data or noise may be removed from the medical summary. However, what is "relevant" to one user may not be relevant to another user for the same patient and may vary with the complexity of the patient and the variety of problems or comorbidities present. For example, when providing a medical summary to a radiologist reading an imaging study for a patient, the radiologist may desire a higher level of inclusiveness based on the degree of hedging, with a relatively low hedging hurdle, for a finding in a prior report, than an application that is presenting discrepancies for a patient with a high hedging hurdle, where the desire may be to minimize false positives leads to including only those medical concepts and/or attributes described with near certainty.

Another example is when a general practitioner is reviewing a patient's records for a chronic condition that is not well controlled (such as heart failure or diabetes), where the clinic or hospital based results are not indicating a cause for the lack of control. The general practitioner may want to open up the tracking to include not just the "official" results but also either automatically reported home monitored results (for example, weight, glucose levels, BP) or the patient self-reported data. Each source of medical data has a different level of not just accuracy but also veracity, and whether the medical data was gathered via a regulated medical device or medical personnel with medical device certification.

When reviewing a patient with a long history of an unresolved complaint, such as chronic pain, there may be many tests that have been performed over weeks, months, or even years and often at multiple facilities. When reviewing the work done so far, a normal summarization, which typically shows only positive findings or results, is inadequate. The user may want to change what is displayed to also see the negative test results to, for example, ascertain what has already been ruled out and potentially by what means when deciding to go for yet more testing, which may also be much more expensive. The ability to change from positive findings to negative findings (or pertinent negative findings), or both, which may have been mentioned on another exam or test, may provide the detail needed by the user but is not provided by current systems.

Another case is in the aggregation of findings that are similar in context but may have varying terminology, such as when reconciling a cardiac patient's problem list. For example, a problem list may include an aortic bicuspid valve, congenital insufficiency of the aortic valve, and aortic valve regurgitation, which may all be categorized together in the problem list. However, when reading a subsequent study looking for prior comparisons, aortic regurgitation data with more specificity may be desired.

The aggregation may take several forms. For example, in some embodiments, an ontology may be used to perform aggregation, such as unified medical language system (UMLS), RSNA produced by Radlex®, systematized nomenclature of medicine—clinical terms (SNOMED-CT), International Classification of Diseases 10$^{th}$ edition (ICD-10), or other internally developed or proprietary ontologies may be used. Tighter aggregation would mean selecting a higher node level in a tree-structured ontology that includes (gathers in) more branches or leaves. For example, a simple and graphical example includes an issue with one of the fingers on the right arm represent a fine granularity of medical data, wherein adjusting the relevancy, aggregating the medical data to also include any issues of the hand, wrist, forearm, elbow, and upper arm as the aggregation is adjusted. In some embodiments, the aggregation does not strictly follow the ontology hierarchy as the aggregation may also have linkage based on laterality. For example, following with the previous example, the next level of aggregation in one direction may be "upper extremity," where both arms are included. This grouping is useful for many types of bilateral comparisons. The aggregation is not limited to simply anatomical structures or body parts. The aggregation may also involve other relationships that may be expressed within an ontology, such as a disease state (for example, children nodes of "Tumor stage finding" in SNOMED-CT), a syndrome (for example, the ongoing efforts within the Disease Ontology community to support cross-walk between disease concepts, genes contributing to disease, and the 'cloud' of associated symptoms, findings and signs), or a treatment (for example, the "Associated Conditions" for specific drugs in DrugBank).

Each of the use cases described above may benefit from the user having the ability to "turn the knob" and interactively adjust the degree of relevancy of extracted findings (extracted medical concepts and associated attributes), whether from clinic visit notes, imaging or surgical reports, discrete data such as vital signs or medications, data gathered form a wide variety of sources such as home health devices via the "internet of things," or self-reported personal records, such as in a weight loss or data collected by a fitness tracker. In some embodiments, the relevancy control described herein may be performed globally or within a specific realm of interest within the presented medical data.

Therefore, there is a need for a dynamic medical summary in which a user may interact with the medical summary to adjust one or more parameters associated with the relevancy of medical data included in the medical summary in order to, for example, filter the results to suit the user's needs at the moment. Accordingly, embodiments described herein provide methods and systems for summarizing medical data by generating a dynamic medical summary that allows a user to tune or adjust one or more parameter associated with the relevancy of medical data included in the medical summary to suit the user's current needs, where there are multiple dimensions of relevancy, such as body part or region, disease state, the source of information, and the like.

Figure 1:
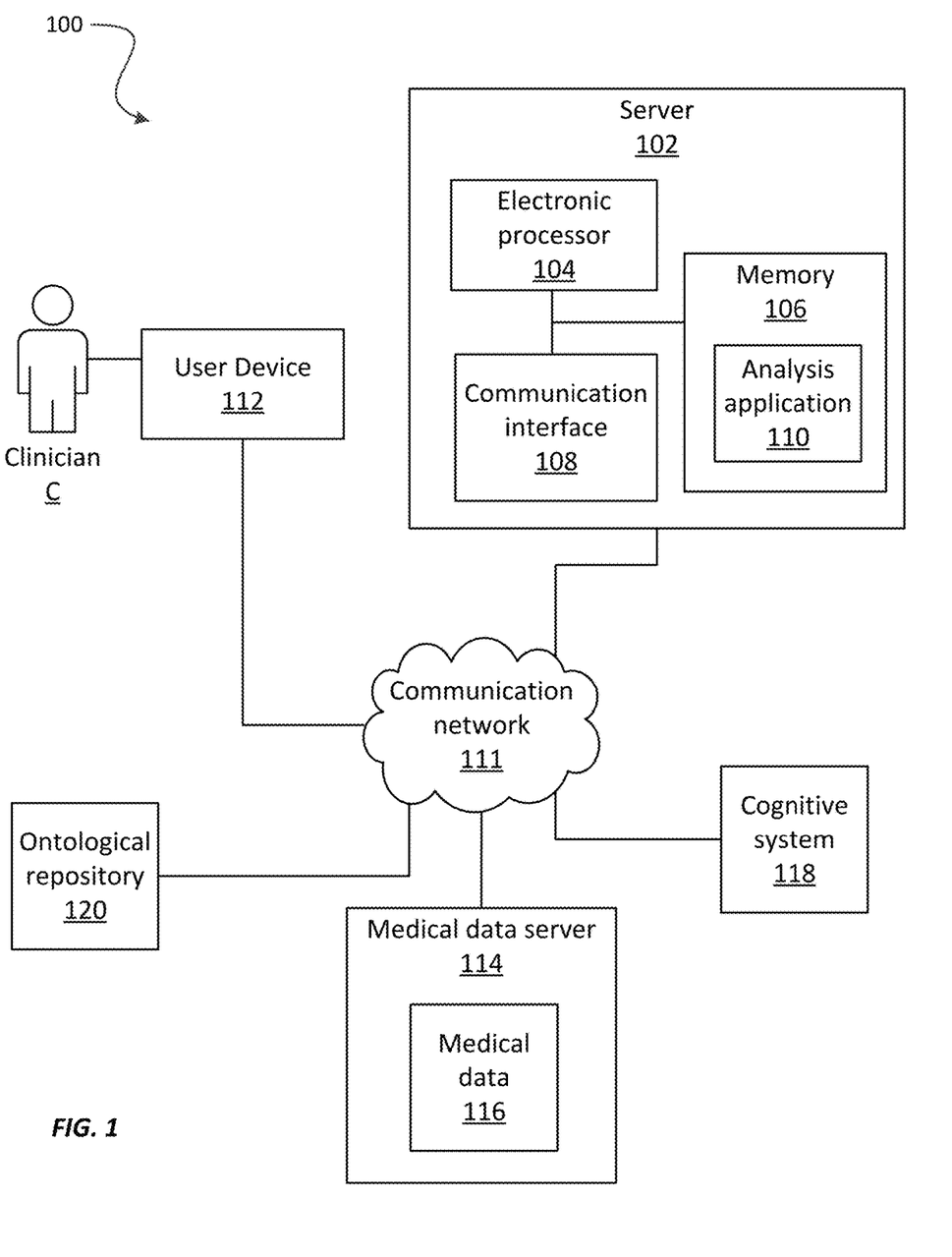
FIG. 1 illustrates a system for summarizing medical data according to some embodiments.

For example, FIG. 1 illustrates a system 100 for summarizing medical data according to some embodiments. The system 100 includes a server 102, a user device 112, a medical data server 114, a cognitive system 118, and an ontological repository 120. Various components of the system 100 communicate via a communication network 111 (for example, the Internet, a local area network (LAN), a wide area network (WAN), and the like). As described in greater detail below, a clinician C interacts with the user device 112 to access various functionality provided by an analysis application 110, which is hosted on server 102. It should be understood that other embodiments of the system 100 may include more, fewer, or different components in different configurations than illustrated in FIG. 1.

The server 102 includes a plurality of electrical and electronic components that provide power, operational control, and protection of the components within the server 102. For example, as illustrated in FIG. 1, the server 102 includes an electronic processor 104 (one or more of a microprocessor, application-specific integrated circuit (ASIC), or another suitable electronic device), a memory 106 (one or more non-transitory, computer-readable storage mediums), and a communication interface 108. The electronic processor 104, the memory 106, and the communication interface 108 communicate wirelessly, over one or more connections or buses, or a combination thereof.

It should be understood that the server 102 illustrated in FIG. 1 represents one example of a server and embodiments described herein may include a server with additional, fewer, or different components than the server 102 illustrated in FIG. 1. In some embodiments, the server 102 performs functionality in addition to the functionality described herein. Similarly, the functionality performed by the server 102 (through execution of instructions by the electronic processor 104) may be distributed among multiple servers (including servers included in a cloud-based computing system or service). Accordingly, functionality described herein as being performed by the electronic processor 104 may be performed by one or more electronic processors included in the server 102, external to the server 102, or a combination thereof. For example, in some embodiments, the functionality described herein (or at least a portion thereof) may be performed by an electronic processor of the user device 112 or as part of a cloud service or environment. Furthermore, systems and components illustrated in FIG. 1 may be combined and distributed in various configurations. For example, in some embodiments, the server 102 may include the cognitive system 118, the ontological repository 120, the medical data server 114, or a combination thereof. Although not illustrated in FIG. 1 or described herein, the user device 112, the medical data server 114, the cognitive system 118, and the ontological repository 120 may include similar components as server 102.

The memory 106 may include read-only memory (ROM), random access memory (RAM) (for example, dynamic RAM (DRAM), synchronous DRAM (SDRAM), and the like), electrically erasable programmable read-only memory (EEPROM), flash memory, a hard disk, a secure digital (SD) card, other suitable memory devices, or a combination thereof. The electronic processor 104 executes computer-readable instructions ("software") stored in the memory 106. The software may include firmware, one or more applications, program data, filters, rules, one or more program modules, and other executable instructions. For example, the software may include instructions and associated data for performing the methods described herein. For example, as illustrated in FIG. 1, the memory 106 may store the analysis application 110 for performing medical record analysis as described herein. It should be understood that the functionality described herein as being performed by the analysis application 110 may be distributed among multiple software components, hardware components, or a combination thereof stored or included in the server 102 or external to the server 102.

The communication interface 108 allows the server 102 to communicate with devices external to the server 102. For example, as illustrated in FIG. 1, the server 102 may communicate with the user device 112, the medical data server 114, the ontological repository 120, the cognitive system 118, or a combination thereof. In particular, the communication interface 108 may include a port for receiving a wired connection to an external device (for example, a universal serial bus (USB) cable and the like), a transceiver for establishing a wireless connection to an external device (for example, over the communication network 111), or a combination thereof. As noted above, FIG. 1 illustrates one example of the system 100 and, in some embodiments, the server 102 may communicate with fewer, additional, or different systems and components than illustrated in FIG. 1. For example, the server 102 may be configured to communicate with multiple medical data servers 114, multiple user devices 112, multiple ontological repositories 120, multiple cognitive systems 118, or a combination thereof.

The ontological repository 120 stores ontological data, such as relationship data for medical events or medical concepts. For example, in some embodiments, the ontological repository 120 includes mapping data for relating and weighting different possible entries in medical records. Example mapping data may be stored, for instance, as one or more look-up tables, as two-dimensional maps, as three-dimensional maps, or a combination thereof.

The cognitive system 118 is a computer system that applies machine learning (artificial intelligence) to mimic cognitive functions, including but not limited to learning and problem solving. Machine learning generally refers to the ability of a computer program to learn without being explicitly programmed. In some embodiments, a computer program (sometimes referred to as a learning engine) is configured to construct a model (for example, one or more algorithms) based on example inputs (training data). Supervised learning involves presenting a learning engine with example inputs and their desired (actual) outputs. The learning engine is configured to learn a general rule (a model) that maps the inputs to the outputs.

The learning engine may be configured to perform machine learning using various types of methods and mechanisms. For example, the learning engine may perform machine learning using decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using some or all of these approaches, the learning engine may ingest, parse, and understand data and progressively refine models for data analytics. Once trained, the learning engine may be referred to as an intelligent system, an AI system, a cognitive system, or the like. Accordingly, in some embodiments, the cognitive system 118 includes Watson® provided by IBM Corporation. The cognitive system 118 may be "trained" using various machine learning techniques. In some embodiments, the cognitive system 118 may be trained using a training set of dynamic medical summaries (training data).

Rather than simply replicating and speeding existing human processes, computers may simultaneously process multiple tasks and draw upon multiple simultaneous information sources based on interactive rules. Therefore, unlike the human brain, which is largely a serial processor, a multi-tasking computer system may simultaneously weigh many factors, and, therefore, complement or exceed human performance with regard to medical record interpretation and analysis.

The medical data server 114 may be associated with one or more entities, such as a particular healthcare provider, a health collaborative, a health maintenance organization (HMOs), or the like. The medical data server 114 includes one or more storage devices that include medical data 116. The medical data 116 may be referred to herein as electronic health record (EHR) data, electronic medical record (EMR) data, or personal health record (PHR) data. The medical data 116 may include images, reports, test results, notes, and other medically-related data for an individual (a patient).

The user device 112 includes an electronic computing device, such as, for example, a terminal, a tablet computer, a laptop computer, a desktop computer, a smart wearable, a smart television or whiteboard, or the like. As noted above, the user device 112 may include similar components as the server 102 (not illustrated herein for sake of simplicity). However, in some embodiments, the user device 112 includes additional, fewer, or different components than the server 102. For example, in some embodiments, the user device 112 includes a display device, such as a screen, monitor, or touchscreen. In some embodiments, the user device 112 also includes an input mechanism, such as a keyboard or keypad, one or more buttons, a microphone, or the like. In embodiments where the user device 112 includes a touchscreen, the touchscreen may function as an input device but, in some embodiments, the user device 112 also includes one or more additional input devices.

Broadly, the clinician C uses the user device 112 to interact with (via, for example, an input mechanism of the user device 112) the analysis application 110 and/or data generated by the analysis application 110, such as a dynamic medical summary. The user device 112 may include software configured to communicate with the server 102 (the analysis application 110 and/or the electronic processor 104 of the server 102) and perform one or more display operations (using, for example, a display device of the user device 112) disclosed herein. For example, the clinician C may use the user device 112 to view a dynamic medical summary generated by the server 102 and interact with the dynamic medical summary to adjust or tune the relevancy of the medical data included in the medical summary.

The user device 112 may include other software applications. Example software applications may enable the clinician C to display an EMR, access a picture archiving and communications system (PACS) or another system or data storage device, or the like. The clinician C may use one or more of the other software applications to provide a contextual link and launch a user interface (UI), such as the dynamic medical summary described herein. The linking may be programmatic or via a UI "scraping" of the other application. That is, the dynamic health record functionalities described herein may be provided via a freestanding UI or linked into, or embedded within, the UI of another larger system, such as that of the EMR.

As described in more detail below, the server 102 (through use of the cognitive system 118, the ontological repository 120, the medical data server 114, or a combination thereof) is configured to generate the dynamic medical summary for display on the user device 112 (a display device of the user device 112). As noted above, the dynamic medical summary provides the clinician C with an overview or summary of the medical data 116 associated with one (or more) patients. As also noted above, the dynamic medical summary is interactive. For example, the clinician C may interact with the dynamic medical summary to expand and contract the medical data 116 included in the medical summary to show more or less data relating to a particular medical concept and/or at least one attribute associated with a particular medical concept included in the medical summary.

As described in more detail below, in some embodiments, to generate the dynamic medical summary, the server 102 is configured to use natural language processing to extract one or more medical concepts and at least one attribute associated with a medical concept from unstructured medical documentation stored in the medical data 116. Example data included in the medical data 116 includes imaging reports, visit notes, surgical notes, discharge summaries, and the like.

In some embodiments, the server 102 also normalizes terminology from extracted text. The server 102 may use one or more ontologies, such as the unified medical language system (UMLS), to map the extracted text to terminology used in the ontology. In some instances, the mapped text from the ontology is mapped to another ontology, such as the SNOMED-CT.

The server 102 may also align the extracted medical concepts (and the at least one attribute associated with the medical concepts) with categories, such as a history of present illness (HPI), social history (personal history), allergies, medications, current findings, and the like. When matching the clinical terms or medical concepts, in some instances, there is no expectation that exact matches are required. For example, within the ontologies, there are lists of synonyms and hierarchical relationships. Matching may be done at the same level of specificity or use the hierarchical relationships to provide better matching (for example, "hand" is part of "arm" or simplistically convert from a brand name to generic medication). To provide better matching across ontologies, additional synonyms may be added to an ontology. Similarly, the AI components used by the server 102 to perform the extraction and mapping may be trained to provide fuzzy matching that is able to conquer inconsistencies in terminology. The ability to match with multiple characteristics or levels of specificity across ontologies, increases the ability (and usefulness) to create linkages (relationships). Additionally other references, such as medication interactions (such as Micromedex or Cerner Multum) or other external reference services, may be used also for linkage definitions.

Figure 2:
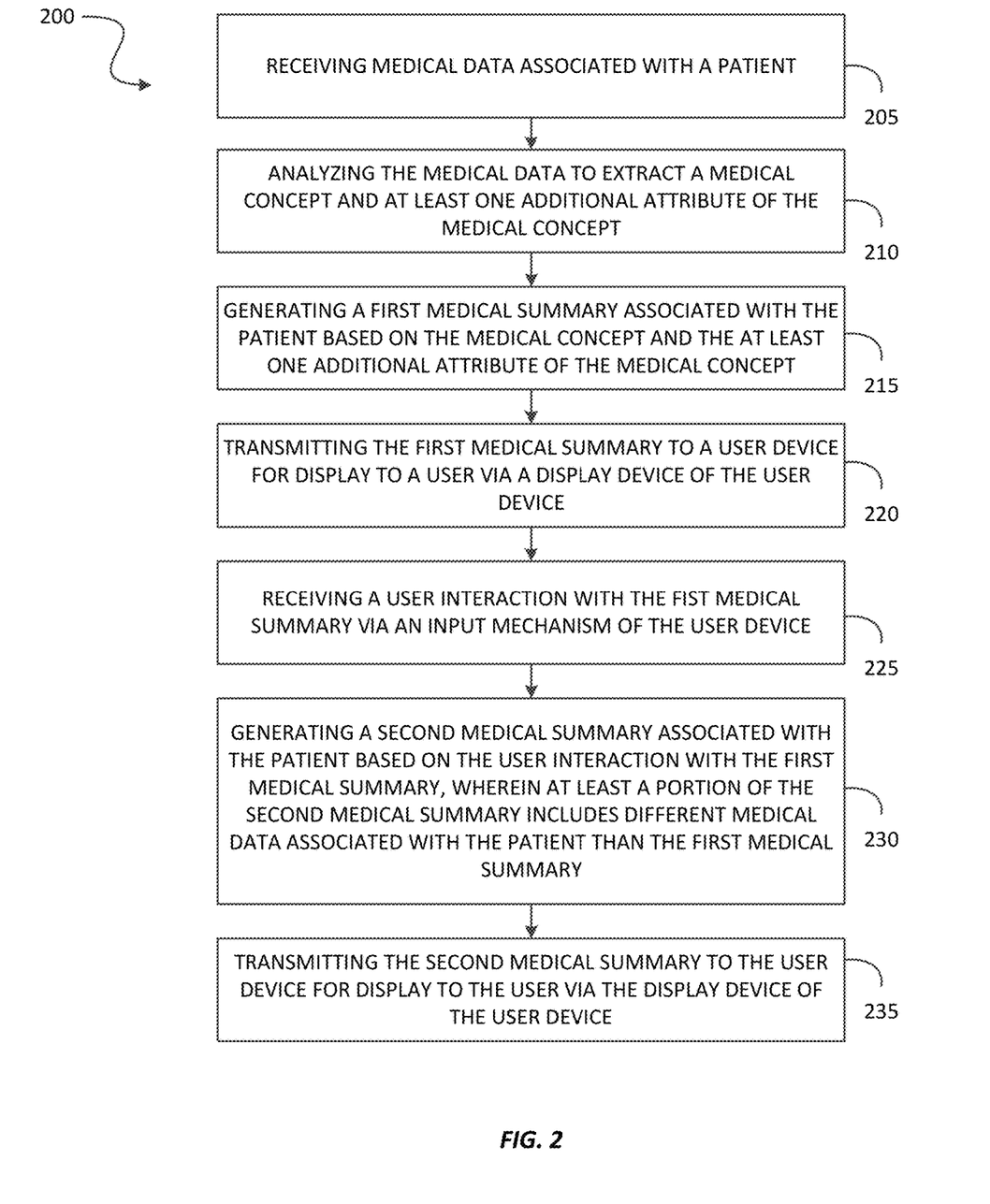
FIG. 2 illustrates a method for summarizing medical data using the system of FIG. 1 according to some embodiments.

For example, FIG. 2 is a flowchart illustrating a method 200 for summarizing medical data according to some embodiments. The method 200 is described here as being performed by the server 102 (via the electronic processor 104 executing instructions). However, as noted above, the functionality performed by the server 102 (or a portion thereof) may be performed by other devices, including, for example, the user device 112 (via an electronic processor executing instructions).

Figure 3:
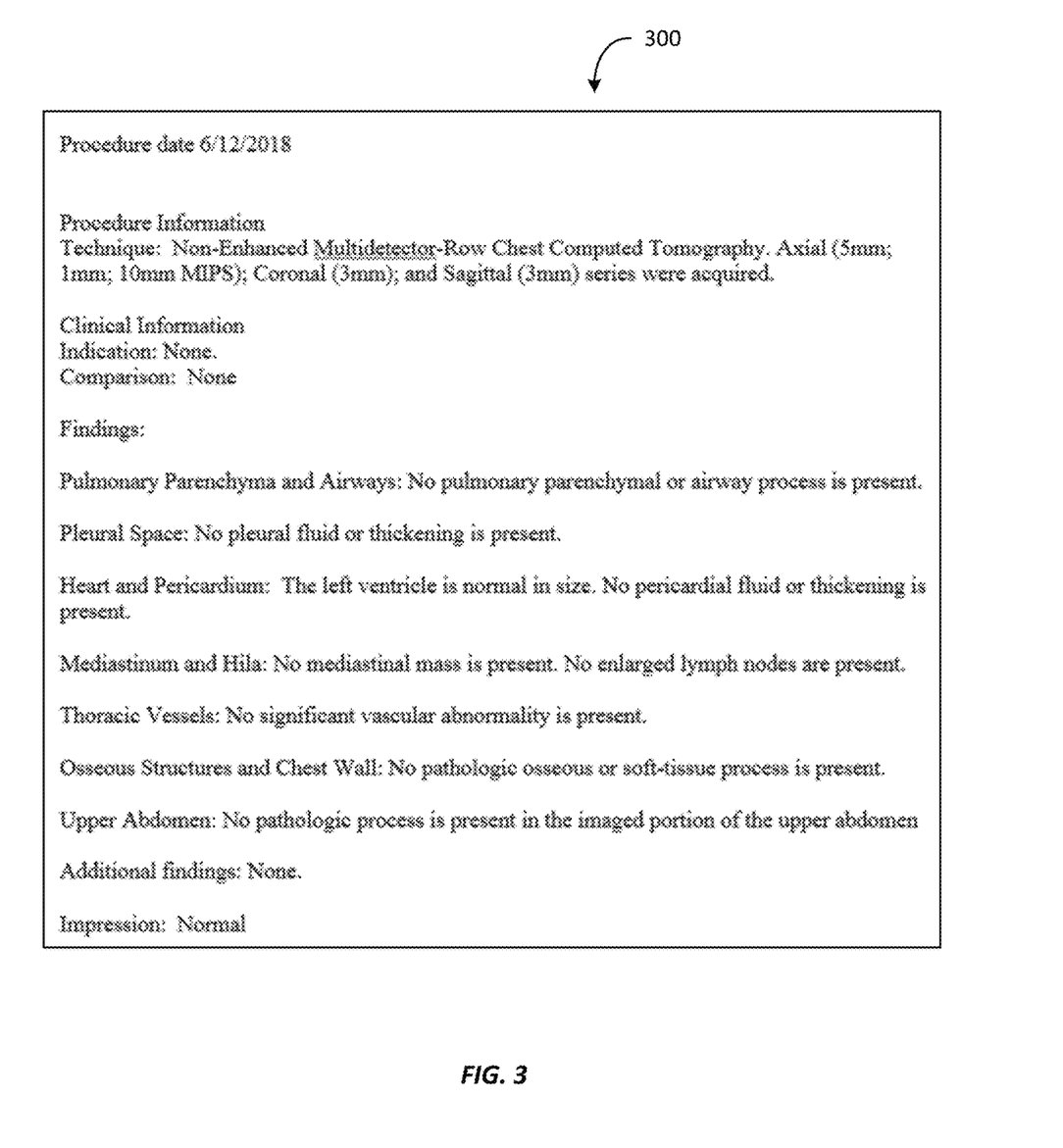
FIG. 3 illustrates an example medical report.

As illustrated in FIG. 2, the method 200 includes receiving medical data associated with a patient (at block 205). In some embodiments, the medical data 116 is stored in the medical data server 114 and is received by the server 102 via the communication network 111. As noted above, the medical data 116 may be aggregated medical data from a plurality of medical sources. Alternatively or in addition, the medical data 116 may include various types of medical data. For example, as illustrated in FIG. 3, the medical data 116 may include medical information included in a medical report 300. The medical report 300 illustrated in FIG. 3 is an example report relating to a CT chest scan without contrast.

After receiving the medical data associated with the patient (at block 205), the server 102 (via the electronic processor 104 and/or the analysis application 110) analyzes the medical data 116 to extract a medical concept and at least one additional attribute of the medical concept (at block 210). For example, the server 102 may analyze the medical data 116 to extract a particular medical finding (the medical concept) and a linkage to or degree of separation of that particular medical finding from the source of that particular medical finding (the at least one additional attribute), where the linkage may indicate that the finding is from a current diagnostic test or report. As another example, the server 102 may analyze the medical data 116 to extract a particular medical finding (the medical concept) and a veracity (or accuracy) of the source of that particular medical finding (the at least one additional attribute), where the veracity may indicate that the medical finding is from a very accurate source, such as a formally calibrated and quality assurance checked lab device.

Analyzing the medical data 116 to extract a medical concept and at least one additional attribute of the medical concept may include applying natural language processing to yield machine-readable text. In some instances, cognitive system 118 includes a natural language processing engine configured to perform natural language processing actions. For example, in some embodiments, the natural language processing is performed to remove "stop words," such as "unspecified" or "not otherwise specified," which are commonly encountered in problem list messages. Alternatively or in addition, in some embodiments, extracting the medical concept and the at least one additional attribute of the medical concept includes optical character recognition (OCR) operations depending on the nature of the files in the electronic health data (for example, the medical data 116). Natural language processing may be performed using methods known in the art.

Alternatively or in addition, in some embodiments, the medical concept and the at least one additional attribute of the medical concept are extracted using one or more ontologies, as described above. In some embodiments, the server 102 (via the electronic processor 104 and/or the analysis application 110) analyzes the medical data 116 with a model developed using machine learning, as described above.

For example, in some embodiments, the extracted medical data is mapped to normalized terms in one or more ontologies. Mapping to one or more ontologies provides the ability to normalize the terminology and add relationships across the concepts. For example, linking of a drug, such as metaprolol, being prescribed to treat a patient's hypertension. Mapping extracted medical data may include leveraging the cognitive system 118 to perform the mapping analysis. In some instances, there may be one or more periods where the cognitive system 118 is trained using training data. Various ontologies may be used during the mapping, such as UMLS and SNOMED-CT.

In some embodiments, after the extracted medical data is mapped, one or more relationships among the data are determined. As an example, determining relationships may include identifying, for each issue or entry in the extracted medical data, which other issues or entries are related to that entry, a relative timeline, whether there are subsequent actions or entries addressing or resolving that entry. In some instances, determining relationships includes identifying connections that require clinician follow-up, such as identifying unresolved, unidentified, or unaddressed medical issues or recommended follow-up diagnostic procedures that have not been performed. In some instances, determining relationships may include determining trust rankings for one or more entries in the extracted medical data. In some embodiments, the cognitive system 118 determines the relationships.

Based on the generated relationships, a relationship map may be generated. In some instances, the relationship map may be stored in a database accessible by the server 102 and/or the user device 112. Generally, the relationship map includes data about connections between entries in the dynamic medical summary and data usable for displaying the map on a UI.

Based on the medical concept and the at least one additional attribute of the medical concept, the server 102 (via the electronic processor 104) generates a first medical summary associated with a patient (at block 215). After generating the first medical summary, the server 102 transmits the first medical summary to the user device 112 for display to a user (for example, the clinician C) via a display device of the user device 112 (at block 220). As noted above, the server 102 is configured to present the medical data 116, or cause the medical data 116 to be displayed via a display device of the user device 112, in a summary form, such as a dynamic medical summary (for example, the first medical summary), so that the clinician C may view an overview of the medical data 116 associated with the patient. In other words, the medical summary may be presented as part of a UI displayed on the user device 112.

The method 200 also includes receiving (over the communication network 111) a user interaction with the first medical summary via an input mechanism of the user device 112 (at block 225). As noted above, the dynamic medical summary is interactive. For example, the clinician C may interact with the medical summary (for example, the first medical summary) to expand and contract the medical data 116 included in the medical summary to show more or less data relating to a particular medical concept and/or at least one attribute associated with a particular medical concept included in the medical summary. The user interaction may include a selection of one or more parameters relating to a relevancy of the medical data 116 included in the dynamic medical summary (for example, the first medical summary). In other words, the content (the medical data 116) included in the dynamic medical summary is varied based on a selection of a user (for example, the clinician C).

Based on the user interaction, the server 102 (via the electronic processor 104) generates a second medical summary associated with the patient (at block 230). In some embodiments, at least a portion of the second medical summary includes (at least some) different medical data associated with the patient than the first medical summary. After generating the second medical summary (at block 230), the server 102 transmits the second medical summary to the user device 112 for display to the user (for example, the clinician C) via the display device of the user device 112 (at block 235).

Figure 4:
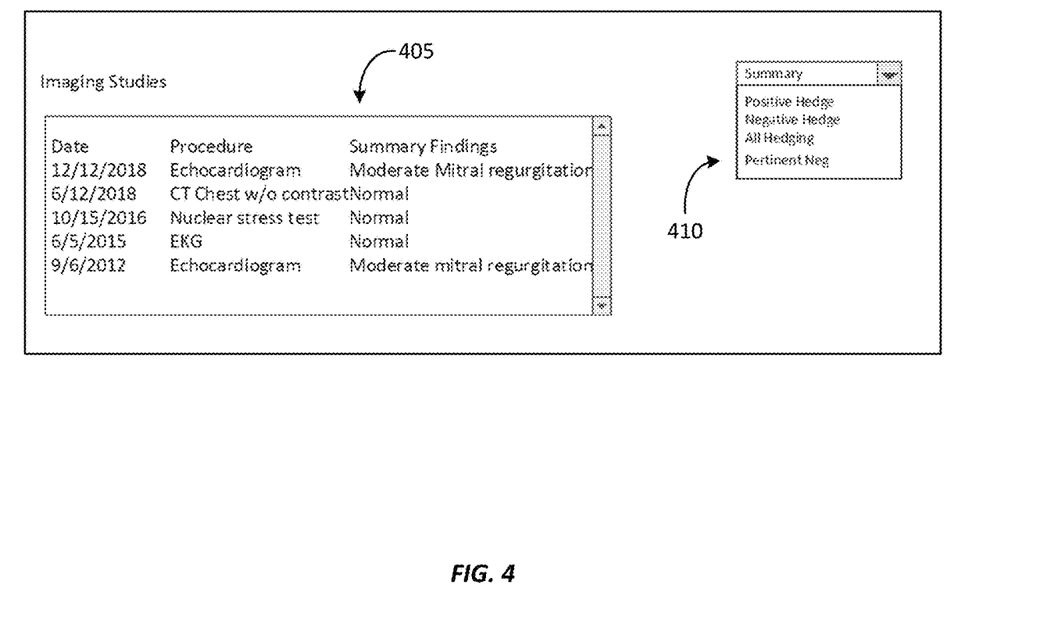
FIG. 4 illustrates an example display of a dynamic medical summary according to some embodiments.

FIG. 4 illustrates a sample dynamic medical summary (for example, the first medical summary) based on the medical data 116 included in the medical report 300 of FIG. 3. As illustrated in FIG. 4, the dynamic summary 400 includes a medical summary window 405 that provides a summary of the medical data 116 associated with the patient. The dynamic medical summary also includes a selection mechanism 410. A user (for example, the clinician C) may user the selection mechanism 410 to input a selection of one or more parameters relating to a relevancy of the medical data 116 included in the dynamic medical summary (for example, the first medical summary). The selection mechanism 410 may be a slider, a dial, a drop-down mechanism, another type of selection mechanism, or a combination thereof. The selection levels may be thought of as discrete or continuous with rankings applied. In some embodiments, there are default settings that are configured for each of these adjustable items. For example, in some embodiments, the first medical summary is generated based on default settings that are configured for each of these adjustable items (a default medical summary) while the second medical summary may be generated based on one or more settings adjusted by a user (an adjusted medical summary).

As illustrated in FIG. 4, the user may interact with the medical summary 400 using a selection mechanism 410 of the medical summary 400. With respect to the illustrated example, the selections may include "Impression" or "Summary," "Positive Hedge," "Negative Hedge," "All Hedging," "Pertinent Neg." (meaning "include pertinent negatives"), or the like. For example, the user may use the selection mechanism 410 to select "Negative Hedge" as a parameter to adjust the relevancy of the medical data included in the medical summary window 410. Accordingly, the display is then updated in the example to include "no significant vascular abnormalities is present." This is an example of a slight amount of hedging, which does not rule out all vascular abnormalities.

Figure 5:
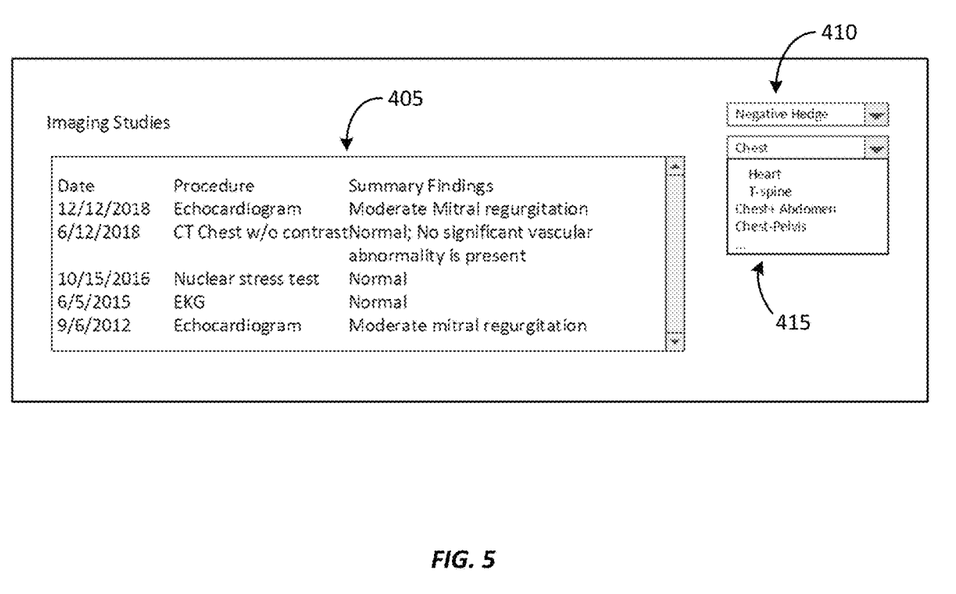
FIG. 5 illustrates an example display of a dynamic medical summary according to some embodiments.

In some embodiments, the dynamic medical summary includes a second selection mechanism 415, as illustrated in FIG. 5. In the illustrated example of FIG. 5, the user may interact with the second selection mechanism 415 to select an additional or second parameter to further adjust the relevancy of the medical data included in the medical summary window 410. As illustrated in FIG. 5, the additional or second parameter relates to a body region and is displayed as a hierarchical tree. In this case, "Heart" is contained within "Chest." As illustrated in the medical summary window 410 of FIG. 5, the medical data 116 relating to an EKG is now included in the medical summary window 410, as an EKG relates to "Heart." However, other exams are filtered out of the dynamic medical summary, such as a right wrist x-ray, a Lumbar spine MM, an x-ray of the patient's sinuses, which were originally included in the medical report 300 of FIG. 3. In some embodiments, the second selection mechanism 415 may be available based on the option selected via the first selection mechanism 410. Similarly, in some embodiments, the options available via the second selection mechanism 415 may vary based on the option selected via the first selection mechanism 410.

Figure 6A:
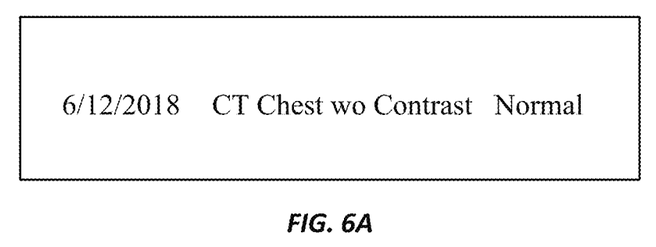
FIGS. 6A-6C illustrate example displays of a dynamic medical summary according to some embodiments.
Figure 6B:
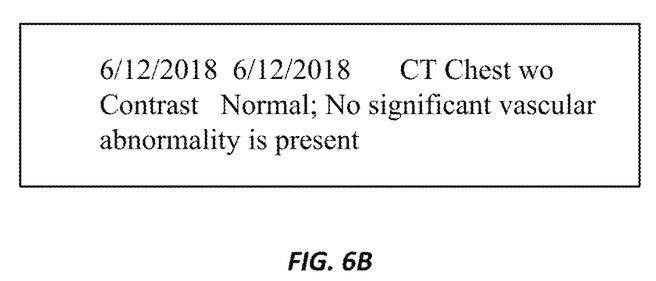
Figure 6C:
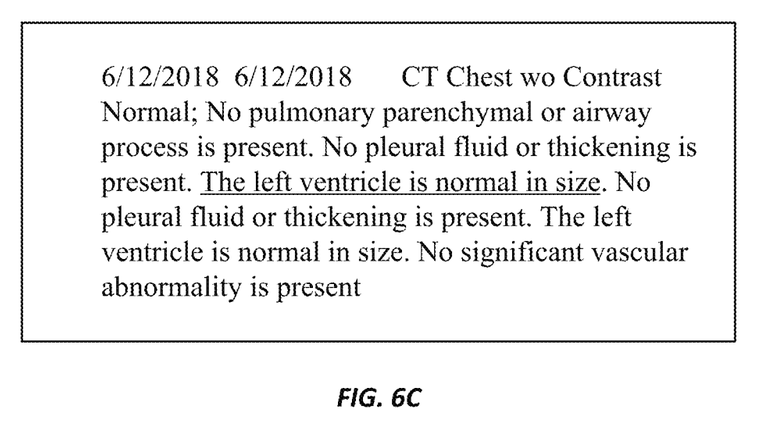

FIGS. 6A-6C illustrate example displays of the dynamic medical summary based on a user interaction (selection). For example, FIG. 6A illustrates the display of the medical summary when the user interaction is a selection of "Impression." FIG. 6B illustrates the display of the medical summary when the user interaction is a selection of "Negative Hedging." FIG. 6C illustrates the display of the medical summary when the user interaction is a selection of "Pertinent Neg."

As illustrated in FIG. 6C, the phrasing "left ventricle is normal in size" is highlighted (underscored). While this is a pertinent negative finding, it is incomplete as the other chambers of the heart are not mentioned. The determination of the incompleteness of the finding may be based on either an ontology where the heading heart is used for the top of the branch and the level of the LV down from it would be searched for peer nodes (for example, Right Ventricle, Right Atrium, and Left Atrium) and if they are not mentioned, but LV is, then the finding would be highlighted as incomplete. An alternative to this is to train the system on "standard report contents" and the expected anatomy to be noted in a standard report. Automatically highlighting the lack of completeness makes it more detectable in the block of text. This automatic highlighting may also be applied if the user selects the display of the entire original report rather than the collapsed summary.

One of the differentiating features of the embodiments described herein is not merely to determine before hand whether or not to include hedging or even the ability to assign hedging terms as positive or negative findings or variability of severity teams for the same purpose, but rather that this may be done in an interactive manner. This allows a user to effectively dig into the data when they need more than the standard summary or to cope with reporting physicians that over-use hedging. Hedging may apply to any written report (for example, office visits, physical therapy notes, surgical notes, as well as imaging or pathology reports).

The type of adjustable selection(s) may vary based on the context of the type of medical data being presented within the medical summary. For example, in the case of vital signs, the adjustments may include the amount of deviation from normal, (for example, "Show all," "Show BP outside of normal range," and the like) and/or a veracity or accuracy, such as "Clinician measured" (which may be a default selection), "auto monitored" (for example, medical data from devices such as an automated blood pressure monitoring system in a hospital), "home monitored," "self-reported" (for example, medical data from a fitness tracker, a smart watch, or other wearable device), and the like. For any set of displayed items, there may be multiple dimensions of adjustability of the associated relevancy criteria.

In some embodiments, as the selection is adjusted (via one or more user interactions), the medical data displayed in the dynamic summary may change (in real-time or pseudo real-time). For example, the use of "self-reported" or "home monitored" data may be useful in the case of blood pressure where a patient may suffer from "white coat syndrome" and have elevated blood pressure during an office visit versus the range of values seen at home. Adjusting for the display of outliers may reduce the number of "normal readings" so that frequency of occurrence or correlation of events may be more easily discerned (for example, for a patient complaining of dizziness or fainting, low blood pressure events started shortly after prescribing or adjusting the dose of a diuretic).

In some embodiments, the server 102 receives multiple user interactions with the dynamic medical summary and generates multiple iterations of the dynamic medical summary based on the multiple user interactions (for example, a first medical summary, a second medical summary, a third medical summary, a fourth medical summary, and the like). For example, the server 102 may receive a second user interaction with the second medical summary and generate a third medical summary associated with the patient based on the second user interaction with the second medical summary. In some embodiments, at least a portion of the third medical summary includes different medical data associated with the patient than the first medical summary and/or the second medical summary. After generating the third medical summary, the server 102 may transmit the third medical summary (via the communication network 111) to the user device 112 for display to the user (for example, the clinician C) via the display device of the user device 112.

Alternatively or in addition, in some embodiments, the server 102 is configured to identify a characteristic of a user (for example, the clinician C) and generate the dynamic medical summary (for example, the first medical summary or the second medical summary) based on the characteristic of the user. As noted above, what is relevant to one user may not necessarily be relevant to another user. For example, the medical data 116 of interest to a radiologist may not be the same medical data 116 of interest to a general practitioner. Accordingly, the server 102 may identify a characteristic, such as an identity or position, of the user and generate the dynamic medical summary based on that characteristic of the user. Alternatively or in addition to the role or specialty of a user, a user may also store personal preferences to set initial filtering of the dynamic medical summary.

In some embodiments, the user interaction with the first medical summary includes a selection of a body part, a body region, a disease state (for example, new, healing, progressing, and the like), or a combination thereof. There are spatial and anatomical relationships that may be linked in a hierarchy within a tree type structure in an ontology. A common example for expanding body part based relevancy is when searching for comparison imaging studies. For example, in the case of a current x-ray study of a shoulder, which shows some abnormalities, the desire may be to see whether these abnormalities are new, progressing, or healing. When searching for prior comparisons, a reading radiologist may wish to also include studies of "nearby" structures (or body regions) that may encompass the shoulder. For example, the reading radiologist may wish to include a chest x-ray, a clavicle, a neck, a Thoracic Spine, and an upper extremity exam in the list of included studies, as many times these exams also frequently encompass the shoulder. In some embodiments, this may require a new or proprietary ontology rather than relying on, for example, "the adjacent to relationship" of UMLS. Accordingly, the user may adjust the relevancy of the medical data included in the dynamic medical summary based on a body part, a body region, a disease state, or a combination thereof.

In some embodiments, the user interaction with the first medical summary includes a selection of a criticality level. The criticality level may relate to a study, a finding, an exam result, and the like. For example, this may be expressed by extraction of a measurement, such as a 90% blockage of the left main coronary artery, order priority based on HL7 priority, critical lab results, descriptive text (such as "morbidly"), and the like. Accordingly, the user may adjust the relevancy of the medical data included in the dynamic medical summary based on a criticality level of a study, a finding, an exam result, or a combination thereof.

There are requirements for critical results communications set forth by various medical societies and/or legally required. However, there is no guarantee that all practitioners or caregivers have been provided this notice (notable issue for hospitalists and others at shift changes). This leads to the desire to then be able to optionally highlight the critical findings when viewing the dynamic medical summary, while not causing "alert fatigue." Accordingly, in some embodiments, the medical data associated with the selected criticality level is highlighted in the dynamic medical summary (for example, in the second medical summary displayed to the user of the user device 112).

In some embodiments, the user interaction with the first medical summary includes a selection of a confidence level, a hedging level, or a combination thereof. Within the reported findings (for example, the medical data 116) there may be varying expressions of the degree of confidence (a confidence level), such as "indicative of," "suggests," "certainly," "could represent," "consistent with," and the like. A hedging level may also vary depending on the training or perceived liability risk by the reading physician. As a result, the hedging scale/ranking (a hedging level) may need to be adjusted by site and likely by the reader. Another setting, whether global or personal, may be to adjust the hedging inclusiveness for particular reporting physicians (for example, Dr. X is notorious for excessive hedging of the majority of the findings in Dr. X's radiology reports). In some embodiments, this would be done in a self-learning manner as the usage patterns of each physician are analyzed versus normal distributions of hedging or certainty within a given patient population or compared to their colleagues. Hedging should not be confused with descriptive gradation where there are accepted terms (which may still need site configuration) that describe the degree of a finding, such as when describing ventricular wall motion in the range from hyperkinetic to dyskinetic. Accordingly, the user may adjust the relevancy of the medical data included in the dynamic medical summary based on a confidence level, a hedging level, or a combination thereof.

In some embodiments, the user interaction with the first medical summary includes a selection of a type of finding, such as a pertinent negative finding, an incidental finding, a critical finding, a primary finding, or a combination thereof. Normal or negative findings are likely to be suppressed in a synoptic view as displaying all of the normal findings would add clutter, which may minimize the ability of the user to pick out the relevant positive findings that the user is most likely interested in. This is, for example, especially true given the time pressures for a reading radiologist churning through over a hundred studies per day. For example, in something as simple as a chest x-ray, the ACR template has three sections of findings and in the CT chest template there are seven sections of findings. However, there are times when reviewing a long and complex history where seeing what is normal helps to guide the next steps and avoid repeated testing versus escalation to the next level of testing. Pertinent negatives should not be confused with "not visualized," "not evaluated," and other statements that exclude a conclusive finding, often due to a dearth of data for the reader. Pertinent negatives were explicitly evaluated and stated as some form of "normal," "unremarkable," or other not abnormal finding. There are also disease terms that superficially appear to be negatives that are not, such as "non-Hodgkins lymphoma," where the negation is instead a modifier of the base term or is part of the base term or category.

Additionally, when a physician is reviewing the results for a test that they ordered, the physician is naturally scanning for confirmation of the reason they ordered the test. Therefore, incidental findings (those items that were discovered as a byproduct of the test) may be unconsciously skipped. The ability to highlight incidental findings on-demand may be attractive to many practitioners and, in some embodiments, this may be linked to highlighting critical results. A further subdivision of the findings is "ordinary findings," which are contained in a body of the report, versus the findings that have been promoted to be part of an "Impressions" section, a "Summary" section, or a "Follow-up Recommendations" section of the report.

Accordingly, the user may adjust the relevancy of the medical data included in the dynamic medical summary based on a type of finding. Alternatively or in addition, in some embodiments, the medical data associated with the type of finding is highlighted in the dynamic medical summary (for example, in the second medical summary displayed to the user of the user device 112).

As noted above, the medical data 116 may be aggregated from a plurality of medical sources. Examples of medical sources include (a) a clinician gathering a measurement from, for example, a formally calibrated and quality assurance checked lab device, such as a blood analyzer measuring glucose; (b) a wearable medical device, such as a closed loop insulin delivery system; (c) a "smart watch" or other wearable device for automated monitoring; (d) a home glucose meter with test strips where readouts are manually logged by the user; and the like. Each source has a varying degree of accuracy of the measurement itself, the methodology of capture, and the methodology of transmission that may potentially degrade the medical information provided, such as in the case of a series of blood glucose readings for treatment of diabetes. There are many other cases where this may vary whether it is reporting of social or family history, medication history, allergy reconciliation, and the like. Another example is for an iodinated contrast allergy where the patient that is injected has a reaction at the facility and this is recorded versus a vague recollection of a childhood reaction to "dye," contrast, or iodine as reported by a family member. Therefore, in some embodiments, the user interaction with the first medical summary includes a selection of a veracity of source level (or an accuracy of source level). Accordingly, the user may adjust the relevancy of the medical data included in the dynamic medical summary based on a veracity of source level (or an accuracy of source level). To further handle non-specific terminology used by lay persons, the additional linkages and selectivity based on the related events (for example, allergic reaction to "dye" when the patient was in a "scanner") may be further refined once a type of study is identified (for example, CT, MR, or PET) and then dye would be logically iodinated for CT or gadolinium based for MR.

In some embodiments, the user interaction with the first medical summary includes a selection of a degree of separation, such as a degree of separation of the finding from the medical source. For example, "history items" are carried forward in many clinical documents (medical records). A degree of separation may be akin to, for example, the concepts of first hand knowledge versus hearsay. In some embodiments, the degree of separation may include the following three degrees of separation: (1) a finding of the current diagnostic test and report; (2) a history item contained in the report with a reference to the source report; and (3) a history item contained in a history of present illness (HPI) or a social history with no reference to the original medical source. It should be understood that the selection of a degree of separation is different from existing ideas for "provenance" of findings as it not only allows the reference to the original document/message but also the clinical quality, as in many cases history information is simply cut and pasted into each new report without a lot of checking or reference to the medical source. In some embodiments, the history items rating (degree of separation) may vary over time, such as when a patient's verbal history of a disease or defect is further confirmed by a clinician. A related concept in the degree of separation is the recommendation for or the ordering of a specific test. The recommendation may be followed and be linked to an order, a study, an exam, and a report. Alternatively or in addition, the recommendation may only have partial ability to be linked, as the follow-up may never have occurred or was performed at another unaffilliated institution (for example, a recommendation for lumbar spine MRI that would often be performed at an outpatient or ambulatory imaging center due to cost or convenience reasons). Accordingly, the user may adjust the relevancy of the medical data included in the dynamic medical summary based on a degree of separation of a finding from an associated medical source.

In addition to the spatial relationships (for example, "adjacent to" in UMLS, "is regional part of" in FMA, and "has regional part" in FMA) useful for aggregation by anatomical structures, there are other non-hierarchical relationships defined in UMLS and alternative ontologies. The other non-hierarchical relationships may include those between diseases and syndromes (for example, associated symptoms in DO) and between treatments and diseases (for example, "manages/treats/prevents" in UMLS and "associated conditions" in DrugBank). These non-hierarchical relationships may be used to uncover more of the relevant patient information. For example, in the emergency department, a patient complains of chest and back pain and has a family history of heart disease. Following a negative ECG, a physican may consider ordering a CT scan. Access to the relevant patient information, diagnoses (for example, past repeated urinary tract infections (UTIs)), and medications (for example, Levaquin) would reveal the patient likely has a bacterial infection, which would avoid ordering of the more expensive tests. Leveraging semantic relationships among diseases, symptoms, and treatments would allow an auto-expanded search and improved hit rate when only partial information is available in patient records.

With respect to clarifying terminology used relating to the methods and systems described herein, "highlighting" refers to bringing forth an item within the UI or other presentation, and is not limited to highlighting by color, reverse font, bold, reordering of a list, or other means. It should be understood that there are multiple ways to bring focus to an item and that the term "highlighting" is used as the generic phrase throughout. Additionally, concept extractions performed by natural language processing may include "findings," which are specific items cited in a report, impressions, or summarizations, anatomical locations and body parts, diseases disease groupings categories or syndromes, and the like. The term "findings" is used throughout to refer to all of these as an example and not a restriction.

Accordingly, embodiments described herein allows relevancy to be adjusted to account for the fact that what is relevant to a physician for a given patient or study may vary depending on complexity or the stage of treatment may vary over time or in different settings. Furthermore, embodiments described herein allow core text analytics and concept extraction to be performed once and the results may be shared across applications to reduce computational cost. For example, the tuning for false positive versus true positive or negative findings may vary by application, but the embodiments described herein allow the core text analytics and concept extraction to be performed once and shared across the applications.

For example, extracting relevant information on a per-application basis (for example, using artificial intelligence functionality) is computationally expensive and inefficient (as many applications may be searching for and extracting the same terms but applying different criteria to the relevancy or importance of a particular finding and displaying them differently). For example, when providing a summary to a radiologist reading an imaging study for a patient, the desire may be for a higher level of inclusiveness based on the degree of hedging with a relatively low hedging hurdle for a finding in a prior report as compared to providing a summary presenting discrepancies for a patient with a high hedging hurdle, where the desire is to minimize false positives leads to including only those items described with near certainty. However, in the embodiments described herein, applications may share the generated additional attributes, which may be applied as needed to generate appropriate user output. Furthermore, these attributes may be reused when different levels of relevancy are requested by the user, such as for providing a reading physician's synoptic view of a patient history versus reconciling a problem list or coding for billing. In other words, related attributes are extracted and stored when a medical report or other medical source is initially analyzed. It is too time consuming to reprocess the medical report or other medical source with different criteria later when a user wants to adjust one or more relevancy parameters. Accordingly, one object of the embodiments described herein is to provide real time updates of a synopsis as a user adjusts one or more of the relevancy controls. Alternatively or in addition, a user may simultaneously loosen one relevancy parameter (for example, hedging or negation) and tighten another (for example, body part or syndrome selection) to drill into a particular issue. Again, this results in more efficient data processing and use of computing resources.

Various features and advantages of the embodiments described herein are set forth in the following claims.

What is claimed is:

1. A system of summarizing medical data, the system comprising:
at least one electronic processor configured to
receive medical data associated with a patient,
analyze the medical data to extract a medical concept and a plurality of additional attributes of the medical concept,
store the medical concept and the plurality of additional attributes of the medical concept,
generate a dynamic medical summary associated with the patient by accessing the stored medical concept and the stored plurality of additional attributes of the medical concept, the dynamic medical summary including a window for displaying the stored medical concept and at least a first additional attribute included in the stored plurality of additional attributes of the medical concept and further including a selection mechanism,
transmit the dynamic medical summary to a user device for display within a user interface displayed to a user via a display device of the user device,
receive a user interaction with the window of the dynamic medical summary via the selection mechanism, the user interaction via the selection mechanism adjusting parameters of at least one of the stored medical concept and at least the first additional attribute included in the stored plurality of additional attributes of the medical concept,
update, in response to receiving the user interaction, the window of the dynamic medical summary within the user interface to display the adjusted stored medical concept and the adjusted first additional attribute included in the stored plurality of additional attributes of the medical concept, wherein at least a portion of the updated window of the dynamic medical summary includes different medical data than the window of the dynamic medical summary before receiving the user interaction.

2. The system of claim 1, wherein the user interaction includes a selection of the second additional attribute included in the stored plurality of additional attributes of the medical concept.

3. The system of claim 1, wherein the medical concept and the plurality of additional attributes of the medical concept are extracted from the medical data using natural language processing.

4. The system of claim 1, wherein the medical concept and the plurality of additional attributes of the medical concept are extracted from the medical data using one or more ontologies.

5. The system of claim 1, wherein the medical data is aggregated from a plurality of medical sources.

6. The system of claim 1, wherein the at least one electronic processor is further configured to identify a characteristic of the user and generate the dynamic medical summary based on the characteristic of the user.

7. The system of claim 1, wherein the user interaction includes a selection of a body region and wherein the window of the dynamic medical summary after the user interaction includes medical data associated with the selected body region.

8. The system of claim 1, wherein the user interaction includes a selection of a disease state and wherein the window of the dynamic medical summary after the user interaction includes medical data associated with the selected disease state.

9. The system of claim 1, wherein the user interaction includes a selection of a criticality level and wherein the window of the dynamic medical summary after the user interaction includes medical data associated with the selected criticality level.

10. The system of claim 9, wherein the medical data associated with the selected criticality level is highlighted in the second medical summary.

11. A method of summarizing medical data, the method comprising:
receiving medical data associated with a patient;
analyzing, with an electronic processor, the medical data to extract a medical concept and a plurality of additional attributes of the medical concept;
storing the medical concept and the plurality of additional attributes of the medical concept;
generating, with the electronic processor, a dynamic medical summary associated with the patient by accessing the stored medical concept and the stored plurality of additional attributes of the medical concept, the dynamic medical summary including a window for displaying the stored medical concept and at least a first additional attribute included in the stored plurality of additional attributes of the medical concept and further including a selection mechanism;
transmitting, with the electronic processor, the dynamic medical summary to a user device for display within a user interface displayed to a user via a display device of the user device;
receiving a user interaction with the window of the dynamic medical summary via the selection mechanism, the user interaction via the selection mechanism adjusting parameters of at least one of the stored medical concept and at least the first additional attribute included in the stored plurality of additional attributes of the medical concept;
updating, with the electronic processor in response to receiving the user interaction, the window of the dynamic medical summary within the user interface to display the adjusted stored medical concept and the adjusted first additional attribute included in the stored plurality of additional attributes of the medical concept, wherein at least a portion of the updated window of the dynamic medical summary includes different medical data than the window of the dynamic medical summary before receiving the user interaction.

12. The method of claim 11, wherein analyzing the medical data to extract the medical concept and the plurality of additional attributes of the medical concept includes analyzing the medical data with a model developed using machine learning.

13. The method of claim 11, wherein receiving the user interaction with the window of the dynamic medical summary includes receiving a selection of a hedging level and wherein updating the window of the dynamic medical summary includes updating the window of the dynamic medical summary to include medical data associated with the selected hedging level.

14. The method of claim 11, wherein receiving the user interaction with the window of the dynamic medical summary includes receiving a selection of a type of finding, the type of finding including at least one selected from a group consisting of a pertinent negative finding, an incidental finding, a critical finding, and a primary finding, and wherein updating the window of the dynamic medical summary includes updating the window of the dynamic medical summary to include medical data associated with the selected type of finding.

15. The method of claim 11, wherein generating the dynamic medical summary associated with the patient includes generating a default medical summary based on default settings, updating the window of the dynamic medical summary associated with the patient includes updating an adjusted medical summary based on the user interaction.

16. A non-transitory, computer-readable medium storing instructions that, when executed by an electronic processor, perform a set of functions, the set of functions comprising:
receiving medical data associated with a patient;
analyzing, with an electronic processor, the medical data to extract a medical concept and a plurality of additional attributes of the medical concept;
storing, with the electronic processor, the medical concept and the plurality of additional attributes of the medical concept;
generating, with the electronic processor, a dynamic medical summary associated with the patient by accessing the stored medical concept and the stored plurality of additional attributes of the medical concept, the dynamic medical summary including a window for displaying the stored medical concept and at least a first additional attribute included in the stored plurality of additional attributes of the medical concept and further including a selection mechanism;
transmitting, with the electronic processor, the dynamic medical summary to a user device for display within a user interface displayed to a user via a display device of the user device;
receiving a user interaction with the window of the dynamic medical summary via the selection mechanism of the user device, the user interaction via the selection mechanism adjusting parameters of at least one of the stored medical concept and at least the first additional attribute included in the stored plurality of additional attributes of the medical concept;
updating, with the electronic processor in response to receiving the user interaction, the window of the dynamic medical summary within the user interface to display the adjusted stored medical concept and the adjusted first additional attribute included in the stored plurality of additional attributes of the medical concept, wherein at least a portion of the updated window of the dynamic medical summary includes different medical data than the window of the dynamic medical summary before receiving the user interaction.

17. The computer-readable medium of claim 16, wherein the set of functions further comprises
receiving a second user interaction with the updated window of the dynamic medical summary;
updating the updated window of the dynamic medical summary associated with the patient based on the second user interaction with the updated window of the dynamic medical summary by accessing the stored medical concept and the stored plurality of additional attributes of the medical concept.

18. The computer-readable medium of claim 16, wherein receiving the user interaction with the window of the dynamic medical summary includes receiving a selection of a confidence level and wherein updating the window of the dynamic medical summary includes updating the window of the dynamic medical summary to include medical data associated with the selected confidence level.

19. The computer-readable medium of claim 16, wherein receiving the user interaction with the dynamic medical summary includes receiving a selection of a veracity level associated with a medical source and wherein updating the window of the dynamic medical summary includes updating the window of the dynamic medical summary to include medical data associated with the selected veracity level associated with the medical source.

20. The computer-readable medium of claim 16, wherein receiving the user interaction with the dynamic medical summary includes receiving a selection of a non-hierarchical relationship and wherein updating the window of the dynamic medical summary includes updating the window of the dynamic medical summary based on the selected non-hierarchical relationship.

* * * * *